United States Patent [19]

Villemez et al.

[11] Patent Number: 5,827,934
[45] Date of Patent: Oct. 27, 1998

[54] CYTOTOXIC DIPHTHERIA TOXIN FRAGMENTS

[75] Inventors: Clarence L. Villemez, Laramie, Wyo.; Dean A. Myers, Edmond, Okla.

[73] Assignee: The University of Wyoming, Laramie, Wyo.

[21] Appl. No.: 799,684

[22] Filed: Nov. 22, 1991

Related U.S. Application Data

[63] Continuation of Ser. No. 488,812, Mar. 5, 1990, abandoned, which is a continuation-in-part of Ser. No. 165,213, Mar. 8, 1988, abandoned.

[51] Int. Cl.$^6$ .............................. C07K 1/12; C07K 14/34
[52] U.S. Cl. ......................... 530/409; 530/402; 530/407
[58] Field of Search .................... 530/350, 402, 530/407, 409, 412, 417, 825

[56] References Cited

U.S. PATENT DOCUMENTS

| | | |
|---|---|---|
| 4,033,819 | 7/1977 | Helting . |
| 4,379,145 | 4/1983 | Masuho et al. . |
| 4,620,948 | 11/1986 | Builder et al. . |
| 4,664,911 | 5/1987 | Uhr et al. . |
| 4,675,382 | 6/1987 | Murphy . |

FOREIGN PATENT DOCUMENTS

| | | |
|---|---|---|
| 8503508 | 8/1985 | WIPO . |
| 8702987 | 5/1987 | WIPO . |

OTHER PUBLICATIONS

Kaczorek et al. (1983) Science 221, 855–858.
Bornstein et al (1977) Meth. Enzymol. 47, 132–145.
Murphy et al. (1986) Proc. Natl. Acad. Sci. 83, 8258–62.
Knuth et al. (1987) in "Protein Purification : Micro to Macro"(R. Burgess, ed.) Alan R. Liss, Inc., pp. 279–305.
Phamacia (1984) "Gel Filtration Theory and Practice", Rahms I. Lund, Sweden, pp. 7–11.
Kaczorek et al. (1983) Science 221, 855–858.
Bornstein et al (1977) Meth, Enzymol. 47, 132–145.
Bishai, et al., "Cloning and Expression in *Escherichia Coli* of Three Fragments of Diphtheria Toxin Truncated with Fragment B," *J. Bacteriol.*, vol. 169, No. 4, pp. 1554–1563 (Apr. 1987).
Falmagne, et al., "The Complete Amino Acid Sequence of Diphtheria Toxin Fragment B. Correlation with its Lipid–Binding Properties," *Biochim. Biophys. Acta,* 827, pp. 45–50 (1985).
Colombatti, et al., "Cloned Fragment of Diphtheria Toxin Linked to T Cell–specific Antibody Identifies Regions of B Chain Active in Cell Entry," *J. Biol. Chem.*, vol. 261, No. 7, pp. 3030–3035 (Mar. 5, 1986).
Howell, et al., "Toxicity of Ricin, Diphtheria Toxin and α–Amanitin for *Acanthamoeba castellanii* (1983)," *J. Parasit.*, 70 (6), pp. 918–923 (1984).
Villemez, et al., "Preparation of an Immunotoxin for *Acanthamoeba castellanii*," *Biochem. Biophys. Res. Commun.*, vol. 125, No. 1, pp. 25–29 (Nov. 30, 1984).
Sundan, et al., "Preparation and Properties of Chimeric Toxins Prepared from the Constituent Polypeptides of Diphtheria Toxin and Ricin," *J. Biol. Chem.*, vol. 257, No. 16, pp. 9733–9739 (Aug. 25, 1982).

(List continued on next page.)

*Primary Examiner*—Robert A. Wax
*Attorney, Agent, or Firm*—Scully, Scott, Murphy & Presser

[57] ABSTRACT

This invention relates to a modified diphtheria toxin (DT) and method of preparing the same in which two carboxy-terminal truncated forms of DT are prepared by specific chemical proteolysis generating two new proteins HA51DT and HA48DT which can be chemically linked to a cell specific binding moiety to produce potent cytotoxins. This invention further relates to carboxy terminal peptides formed in accordance with said proteolysis generating three peptides HA11DT, HA7DT and HA3DT.

4 Claims, 3 Drawing Sheets

OTHER PUBLICATIONS

Gilliland, et al., "Antibody–Directed Cytotoxic Agents: use of Monoclonal Antibody to Direct the Action of Toxin A chains to Colorectal Carcinoma Cells," *Proc. Natl. Acad. Sci. USA.* vol. 77, No. 8, pp. 4539–4543 (Aug. 1980).

Boquet, "Transport of Diphtheria Toxin Fragment A Across Mammalian Cell Membranes," *Biochem. Biophys. Res. Commun.,* vol. 75, No. 3, pp. 696–702 (1977).

Falmagne, et al., "Structure–Activity Relationships of the B Fragment of Diphtheria Toxin: The Lipid–Binding Domains," Toxicon, vol. 20, No, 1, pp. 243–246 (1982).

DeLange, et al., "The Amino Acid Sequence of Fragment A, an Enzymically Active Fragment of Diphtheria Toxin," *J. Biol. Chem.,* vol. 254, No. 13, pp. 5838–5842 (July 10, 1979).

DeLange, et al., "The Amino Acid Sequence of Fragment A, an Enzymically Active Fragment of Diphtheria Toxin," *J. Biol. Chem.,* vol. 254, No. 13, pp. 5827–5831 (Jul. 10, 1979).

Drazin, et al., "The Amino Acid Sequence of Fragment A, an Enzymically Active Fragment of Diphtheria Toxin," *J. Biol. Chem.,* vol. 254, No. 13, pp. 5832–5837 (Jul. 10, 1979).

Chang, "The Effect of Diphtheria Toxin B Chain on Toxicity of the Native Toxin and Its A Chain Conjugate to Asialoorosomucoid ," *Toxins I,* Monday PM, 1544.

Audibert, et al., "Active Antitoxic Immunization by a Diphtheria Toxin Synthetic Oligopeptide," *Nature*, vol. 289, p. 593 (Feb. 12, 1981).

Lambotte, et al., "Primary Structure of Diphtheria Toxin Fragment B: Structural Similarities with Lipid–Binding Domains," *J. Cell Biol.,* vol. 87, pp. 837–840 (Dec. 1980).

Diphtheria Toxin

HA51DT

HA48DT

- Enzyme
- Hydrophobic
- Cell binding

FIG. 1

CYTOTOXIC DIPHTHERIA TOXIN FRAGMENTS

This application is a continuation of application Ser. No. 488,812, filed on Mar. 5, 1990, which is a continuation-in-part of application Ser. No. 165,213, filed Mar. 8, 1988 both now abandoned.

FIELD OF THE INVENTION

The present invention is directed to modified diphtheria toxins, and to the method of production thereof, wherein said toxins retain the translocation properties and the potential cytotoxicity of native diphtheria toxin but are devoid of the cell binding moiety present on the B-chain of said native toxin. The present invention is also directed to carboxy terminal peptides of diphtheria toxin wherein said peptides encompass the binding region(s) of said toxin. Moreover, this invention contemplates a method for the production of immunotoxins wherein said immunotoxins are selectively cytotoxic to specific cell types by the linking of binding moieties specific for said cell types to the modified diphtheria toxin.

BACKGROUND OF THE INVENTION

Hybrid proteins having potential as anti-cancer and parasitic disease agents have been prepared by linking the enzymatically active A-chains of catalytic toxins to antibodies, hormones or lectins, thereby allowing specific delivery of the enzyme to desired cell types (Pastan, et al., 1986. *Cell* 47:641–648). These A-chain immunotoxins are sufficiently specific, but have proved insufficiently toxic for use in vivo. A-chain immunotoxins are orders of magnitude less potent than the parent toxins. A diminished escape of A-chain from endocytotic vesicles is apparently responsible for the difference in toxicity (Cassellas, et al., 1984. *J. Biol. Chem.* 259:9559–9364). The B-chains of ricin and diphtheria toxin (DT) have dual activities: first, translocation of their respective A chains to the cytosol (Neville and Hudson, 1986. *Ann. Rev. Biochem.* 55:195–224), and second, cell-surface binding (Olsnes and Sanvig, 1985. *In Endocytosis* eds Pastan and Willingham, Plenum Publ. Corp. pp. 195–230). As translocation appears to be the rate limiting step in intoxication, incorporation of B-chains into immunotoxins may enhance cytotoxicity (Columbatti et al., 1986. *J. Biol. Chem.* 261:3030–3035). However, inclusion of toxin B-chains compromises the selectivity for which the immunotoxins were synthesizes, because of the relatively non-specific B-chain binding sites.

The primary diphtheria toxin membrane-binding property has been localized within a 17 kilodalton carboxy-terminal segment of the B-chain and apparently resides in a domain different from that responsible for the membrane translocation function (Columbatti et al., supra). The translocation property has been partially ascribed to regions of hydrophobicity within the amino terminal 20 kilodaltons of B-chain (Hudson and Neville, 1985. *J. Biol. Chem.* 260:2675–2680). Another region of hydrophobicity with possible translocation involvement is located within the carboxy terminal 17 kilodaltons of B-chain (Hudson and Neville, supra).

Attempts to modify catalytic toxins have been reported. Vitetta et al. 1987. *Science* 238:1098–1104 produced a chloramine-T oxidized ricin B-chain that was devoid of lectin activity, yet could potentiate the cytotoxicity of ricin A-chain containing hybrid toxins. Unfortunately, the modified ricin B-chains were several-fold lower in activity than native ricin B-chain and would no longer associate spontaneously with ricin A-chain. Naturally occurring mutant or genetically engineered forms of DT which lack the carboxy-terminal 17 kilodaltons of B-chain potentiate the cytotoxicity of hybrid toxins prepared with these proteins 100-fold over A-chain containing hybrids, but remain 100-fold less toxic than DT containing hybrids (Columbatti et al., supra). A DT-fusion protein has been produced in which the carboxy-terminal 51 amino acids has been replaced with the alpha MSH (melanocyte stimulating hormone) sequence (Murphy et al., 1986. *Proc. Natl. Acad. Sci., USA,* 83:8258–8262). Experiments with this protein indicate that it is highly toxic to cells expressing the alpha-MSH receptor, and non-toxic to non-target cells. Unfortunately, these and similar genetically engineered proteins appear to be extremely susceptible to protease activity by the expression vector; there also appear to be other expression problems possibly related to proper folding of an active protein (Murphy et al., supra; Bishai et al., 1987. *J. Bacteriol.* 169:1554–1563). Greenfield et al. (1987. *Science* 238:536–539) reported the isolation of mutant forms of DT (CRM 102 and 107) with point mutations in the carboxy terminus at residues 508 (CRM 102) and 525 (CRM 107) that are less toxic to susceptible cells than DT, yet are equally potent as DT when incorporated into a hybrid toxin. No data, however, was reported concerning the speed of toxicity relative to DT for these receptor-deficient toxins.

A major drawback in the development of immunotoxins, and other specific cytotoxic agents, has been the slow rate of killing offered by A-chain conjugates. A-chain immunotoxins are sufficiently selective in vitro, but in vivo results have been poor. Maximal injections of up to 10–20 mg/kg body weight results in a 95% decrease in tumor burden (Fulton et al., 1987. *Fed. Proc.* 461:1507) which is insufficient to cure the animal.

The subject invention relates to modified diphtheria toxins lacking the B-chain cell binding properties resulting in toxins apparently exhibiting no toxicity to cells. Said toxins are produced by selectively removing carboxy terminal peptides encompassing said binding properties while leaving the translocation characteristics of diphtheria toxin intact. However, these toxins, when a cell binding moiety is chemically linked to the truncated B-chain, exhibit potency and fast acting characteristics equivalent to native DT, yet are specific for desired sub-populations of cells. Moreover, these modified toxins can be useful in preparing effective in vivo immunotoxins and other specific cytotoxic agents.

BRIEF DESCRIPTION OF THE DRAWINGS

FIG. 1 is a diagrammatic representation of diphtheria toxin (DT) and its derivatives HA51DT and HA48DT indicating the major functional regions and the two hydroxylamine sensitive asparaginyl-glycyl bonds at positions 453/454 (a) and 481/482 (b). The hydrophobic regions are thought to be primarily involved in membrane translocation.

SUMMARY OF THE INVENTION

Figure 2B:
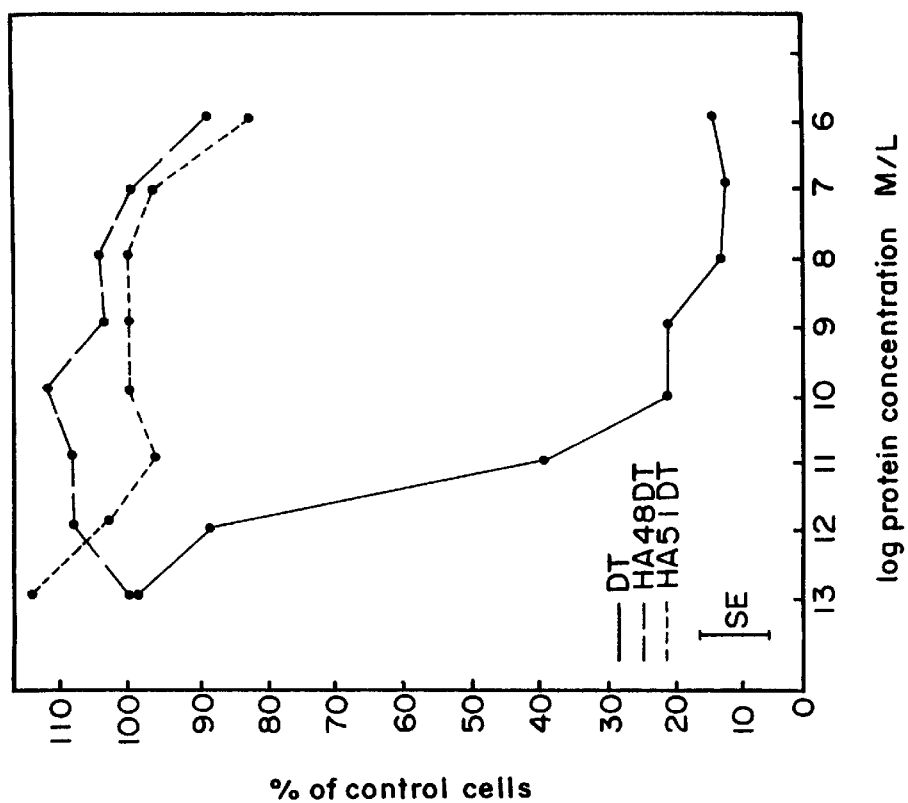
FIG. 2 is a graphical representation of cytotoxicity and binding of diphtheria toxin (DT), HA51DT and HA48DT to MCF-7 human breast cancer cells. Graph (a) represents displacement of $^{125}$I-labeled DT from membranes prepared from MCF-7 cells; Graph (b) represents toxicity of DT, HA51DT and HA48DT to MCF-7 cells.

The subject invention relates to modified diphtheria toxins (DT) wherein said toxins are devoid of the cell binding moiety present on the B-chain of native DT. Moreover, this invention contemplates a method for the preparation of immunotoxins and other specific cytotoxic agents using said modified toxins wherein a specific binding moiety is chemically linked to the truncated B-chain. This invention also contemplates a method for the selective cytotoxicity of numerous cell types including tumor or cancer cells, in vivo.

DETAILED DESCRIPTION OF THE INVENTION

The present invention relates to modified diphtheria toxin, hereinafter referred to as DT. Native DT is characterized by the amino acid sequence shown below:

N*—Gly—Ala—Asp—Asp—Val=Val—Asp—Ser—Ser—Lys—Ser—Phe=Val=Met—Glu—Asn—Phe—Ser—Ser—Tyr—*His*—Gly—

Thr—Lys—Pro—Gly—Tyr—Val—Asp—Ser—Ile—Gln—Lys—Gly—Ile—Gln—Lys—Pro—Lys—Ser—Gly—Thr—Gln—Gly—Asn—

Tyr—Asp—Asp—Asp—Trp—Lys—Gly—Phe—Tyr—Ser—Thr—Asp—Asn—Lys—Tyr—Asp—Ala=Ala—Gly—Tyr—Ser—Val—

Asp—Asn—Glu—Asn—Pro—Leu—Ser—Gly—Lys—Ala—Gly—Gly—Val=Val—Lys—Val—Thr—Tyr—Pro—Gly—Leu—Thr—Lys

Val=Leu=Ala—Leu—Lys—Val—Asp—Asn—Ala—Glu—Thr—Ile—Lys—Lys—Glu—Leu—Gly—Leu—Ser—Leu—Thr—Glu—Pro

Leu=Met—Glu—Gln—Val—Gly—Thr—Glu—Glu—Phe=Ile—Lys—Arg—Phe—Gly—Asp—Gly—Ala—Ser—Arg—Val=Val=Leu—

Ser—Leu=Pro=Phe=Ala—Glu—Glu—Ser—Ser—Ser—Val—Glu—Tyr—Ile—Asn—Asn—Trp—Glu—Gln—Ala—Lys—Ala=Leu=

Ser—Val—Glu—Leu—Glu—Ile—Asn—Phe—Glu—Thr—Arg—Gly—Lys—Arg—Gly—Gln—Asp—Ala=Met—Tyr—Glu—Tyr—

Met=Ala—Gln—Ala—Cys—Ala—Gly—Asn—Arg—Val—Arg—Arg—Ser—Val—Gly—Ser—Ser—Leu—Ser—Cys—

Ile=Asn—Leu—Asp—Trp—Asp—Val=Ile—Arg—Asp—Lys—Thr—Lys—Thr—Lys—Ile—

Glu—Ser—Leu—Lys—Glu—*His*—Gly—Pro=Ile—Lys—Asn—Lys—Met—Ser—Glu—Ser—

Pro—Asn—Lys—Thr—Val—Ser—Glu—Glu—Lys—Ala—Lys—Gln—Tyr—Leu—Glu—Glu—

Phe—*His*—Gln—Thr—Ala=Leu—Glu—*His*—Pro—Glu—Leu—Ser—Glu—Leu—Lys—Thr—Val—

Thr—Gly—thr—Asn—Pro=Val=Phe=Ala—Gly—Ala—Asn—Tyr—Ala=Ala=Trp—Ala=Val—

Asn—Val=Ala=Gln—Val=Ile—Asp—Ser—Glu—Thr—Ala—Asp—Asn—Leu—Glu—Lys—Thr—

Thr—Ala=Ala—Leu—Ser—Ile—Leu=Pro—Gly—Ile—Gly—Ser—Val=Met—Gly—Ile=Ala—Asp—

Gly—Ala=Val—*His*—*His*—Asn—Thr—Glu—Glu—Ile=Val—Ala—Gln—Ser—Ile=Ala=Leu—Ser—

Ser—Leu=Met=Val=Ala—Gln—Ala—Ile=Pro=Leu—Val—Gly—Glu—Leu—Val—Asp—Ile—

Gly—Phe=Ala=Ala—Tyr—Asn—Phe=Val—Glu—Ser—Ile=Ile—Asn—Leu=Phe—Gln—Val=

Val—*His*—Asn—Ser—Tyr—Asn—Arg—Pro=Ala—Tyr—Ser—Pro—Gly—*His*—Lys—Thr—Gln—

Pro=Phe=Leu=His—*Asp*—Gly—Tyr—Ala=Val—Ser—Trp—Asn—Thr—Val—Glu—Asp—Ser—

Ile=Ile—Arg—Thr—Gly—Phe—Gln—Gly—Glu—Ser—Gly—*His*—Asp—Ile—Lys—Ile—Thr—

Ala—Glu—Asn—Thr—Pro=Leu=Pro=Ile=Ala—Gly—Val=Leu=Leu=Pro—Thr—Ile=Pro—Gly

Lys—Leu—Asp—Val—Asn—Lys—Ser—Lys—Thr—*His*—Ile—Ser—Val—Asn—Gly—Arg—

Lys—Ile—Arg—Met—Arg—Cys—Arg—Ala—Ile—Asp—Gly—Asp—Val—Thr—Phe—Cys—

Arg—Pro—Lys—Ser—Pro=Val—Tyr—Val—Gly—Asn—Gly—Val—*His*—Ala—Asn—Leu—*His*—

Val=Ala=Phe—*His*—Arg—Ser—Ser—Ser—Glu—Lys—Ile—*His*—Ser—Asn—Glu—Ile—Ser—

Ser—Asp—Ser—Ile—Gly—Val=Leu—Gly—Tyr—Gln—Lys—Thr—Val—Asp—*His*—Thr—Lys—

Val—Asn—Ser—Lys—Leu—Ser—Leu=Phe=Phe—Glu—Ile—Lys—Ser—C wherein the small print refers to the A chain, the large print refers to the B chain, underlined amino acids are hydrophobic, bold print refers to negatively charged amino acids, heavy bold print refers to positively charged amino acids and italicized amino acids are ionizable histidyl residues that protonize due to protein environment.

The new toxin is devoid of the cell binding moiety associated with the B-chain while retaining the translocation properties of said chain. More particularly, one aspect of this invention is directed to the use of hydroxyamine hydrolysis to break the asparaginyl-glycyl bonds sensitive to such hydrolysis. The B-chain of DT contains two asparaginyl-glycyl bonds at amino acid positions 453–454 and at 481–482. hence, in accordance with the present invention, following hydroxyamine hydrolysis executed under one set of conditions, approximately equal amounts of a 48 kilodalton (Kd) peptide, a 51 Kd peptide and unhydrolyzed DT are produced. Additionally, following said hydrolysis, smaller carboxy terminal amino acid segments (peptides) are produced. These peptides comprise fragments of approximate size 11 Kd, 7 Kd and 3.5 Kd. Hereinafter, said peptides are defined as HA11DT, HA7DT and HA3DT, respectively. One skilled in the art will recognize the utility of said peptides as potential binding site moieties and potential agonists or antagonists for the specific membrane binding site.

The 48 Kd modified diphtheria toxin is further characterized by the following amino acid sequence:

N* — Gly — Ala — Asp — Asp — Val = Val — Asp — Ser — Ser — Lys — Ser — Phe = Val = Met — Glu — Asn — Phe — Ser — Ser — Tyr — *His* — Gly —

Thr — Lys — Pro — Gly — Tyr — Val — Asp — Ser — Ile — Gln — Lys — Gly — Ile — Gln — Lys — Pro — Lys — Ser — Gly — Thr — Gln — Gly — Asn —

Tyr — Asp — Asp — Asp — Trp — Lys — Gly — Phe — Tyr — Ser — Thr — Asp — Asn — Lys — Tyr — Asp — Ala = Ala — Gly — Tyr — Ser — Val —

Asp — Asn — Glu — Asn — Pro — Leu — Ser — Gly — Lys — Ala — Gly — Gly — Val = Val — Lys — Val — Thr — Tyr — Pro — Gly — Leu — Thr — Lys

Val = Leu = Ala — Leu — Lys — Val — Asp — Asn — Ala — Glu — Thr — Ile — Lys — Lys — Glu — Leu — Gly — Leu — Ser — Leu — Thr — Glu — Pro

Leu = Met — Glu — Gln — Val — Gly — Thr — Glu — Glu — Phe = Ile — Lys — Arg — Phe — Gly — Asp — Gly — Ala — Ser — Arg — Val = Val = Leu —

Ser = Leu = Pro = Phe — Ala — Glu — Glu — Ser — Ser — Ser — Val — Glu — Tyr — Ile — Asn — Asn — Trp — Glu — Gln — Ala — Lys — Ala = Leu =

Ser — Val — Glu — Leu — Glu — Ile — Asn — Phe — Glu — Thr — Arg — Gly — Lys — Arg — Gly — Gln — Asp — Ala = Met — Tyr — Glu — Tyr —

Met = Ala — Gln — Ala — Cys — Ala — Gly — Asn — Arg — Val — Arg — Arg — Ser — Val — Gly — Ser — Ser — Leu — Ser — Cys —

Ile = Asn — Leu — Asp — Trp — Asp — Val = Ile — Arg — Asp — Lys — Thr — Lys — Thr — Lys — Ile —

Glu — Ser — Leu — Lys — Glu — *His* — Gly — Pro = Ile — Lys — Asn — Lys — Met — Ser — Glu — Ser —

Pro — Asn — Lys — Thr — Val — Ser — Glu — Glu — Lys — Ala — Lys — Gln — Tyr — Leu — Glu — Glu —

Phe — *His* — Gln — Thr — Ala = Leu — Glu — *His* — Pro — Glu — Leu — Ser — Glu — Leu — Lys — Thr — Val —

Thr — Gly — thr — Asn — Pro = Val = Phe = Ala — Gly — Ala — Asn — Tyr — Ala = Ala = Trp = Ala = Val —

Asn — Val = Ala = Gln — Val = Ile — Asp — Ser — Glu — Thr — Ala — Asp — Asn — Leu — Glu — Lys — Thr —

Thr — Ala = Ala — Leu — Ser — Ile = Leu = Pro — Gly — Ile — Gly — Ser — Val = Met — Gly — Ile = Ala — Asp —

Gly — Ala = Val — *His* — *His* — Asn — Thr — Glu — Glu — Ile = Val = Ala — Gln — Ser — Ile = Ala = Leu — Ser

Ser — Leu = Met = Val = Ala — Gln — Ala = Ile = Pro = Leu = Val — Gly — Glu — Leu = Val — Asp — Ile —

Gly — Phe = Ala = Ala — Tyr — Asn — Phe = Val — Glu — Ser — Ile = Ile — Asn — Leu = Phe — Gln — Val =

Val — *His* — Asn — Ser — Tyr — Asn — Arg — Pro = Ala — Tyr — Ser — Pro — Gly — *His* — Lys — Thr — Gln —

Pro = Phe — Leu = *His* — *Asp* — Gly — Tyr — Ala = Val — Ser — Trp — Asn — Thr — Val — Glu — Asp — Ser —

Ile = Ile — Arg — Thr — Gly — Phe — Gln — Gly — Glu — Ser — Gly — *His* — Asp — Ile — Lys — Ile — Thr —

Ala — Glu — Asn — Thr — Pro — Leu = Pro — Ile = Ala — Gly — Val = Leu — Leu — Pro — Thr — Ile = Pro — Gly

Lys — Leu — Asp — Val — Asn — Lys — Ser — Lys — Thr — *His* — Ile — Ser — Val — Asn —

The 51 Kd modified diphtheria toxin is further characterized by the following amino acid sequence is shown below:

N* — Gly — Ala — Asp — Asp — Val = Val — Asp — Ser — Ser — Lys — Ser — Phe = Val = Met — Glu — Asn — Phe — Ser — Ser — Tyr — *His* — Gly —

Thr — Lys — Pro — Gly — Tyr — Val — Asp — Ser — Ile — Gln — Lys — Gly — Ile — Gln — Lys — Pro — Lys — Ser — Gly — Thr — Gln — Gly — Asn —

Tyr — Asp — Asp — Asp — Trp — Lys — Gly — Phe — Tyr — Ser — Thr — Asp — Asn — Lys — Tyr — Asp — Ala = Ala — Gly — Tyr — Ser — Val —

-continued

Asp—Asn—Glu—Asn—Pro—Leu—Ser—Gly—Lys—Ala—Gly—Gly—Val=Val—Lys—Val—Thr—Tyr—Pro—Gly—Leu—Thr—Lys—
Val=Leu=Ala=Leu—Lys=Val—Asp—Asn—Ala—Glu—Thr—Ile—Lys—Lys—Glu—Leu—Gly—Leu—Ser—Leu—Thr—Glu—Pro—
Leu=Met—Glu—Gln—Val—Gly—Thr—Glu—Glu—Phe=Ile—Lys—Arg—Phe—Gly—Asp—Gly—Ala—Ser—Arg—Val=Val=Leu—
Ser=Leu=Pro=Phe=Ala—Glu—Glu—Ser—Ser—Ser—Val—Glu—Tyr—Ile—Asn—Asn—Trp—Glu—Gln—Ala—Lys—Ala=Leu=
Ser—Val—Glu—Leu—Glu—Ile—Asn—Phe—Glu—Thr—Arg—Gly—Lys—Arg—Gly—Gln—Asp—Ala=Met—Tyr—Glu—Tyr—
Met=Ala—Gln—Ala—Cys—Ala—Gly—Asn—Arg—Val—Arg—Arg—Ser—Val—Gly—Ser—Ser—Leu—Ser—Cys—
Ile=Asn—Leu—Asp—Trp—Asp—Val=Ile—Arg—Asp—Lys—Thr—Lys—Thr—Lys—Ile—
Glu—Ser—Leu—Lys—Glu—His—Gly—Pro=Ile—Lys—Asn—Lys—Met—Ser—Glu—Ser—
Pro—Asn—Lys—Thr—Val—Ser—Glu—Glu—Lys—Ala—Lys—Gln—Tyr—Leu—Glu—Glu—
Phe—His—Gln—Thr—Ala=Leu—Glu—His—Pro—Glu—Leu—Ser—Glu—Leu—Lys—Thr—Val—
Thr—Gly—thr—Asn—Pro=Val=Phe=Ala—Gly—Ala—Asn—Tyr—Ala=Ala=Trp=Ala=Val—
Asn—Val=Ala=Gln—Val=Ile—Asp—Ser—Glu—Thr—Ala—Asp—Asn—Leu—Glu—Lys—Thr—
Thr—Ala=Ala—Leu—Ser—Ile=Leu—Pro—Gly—Ile—Gly—Ser—Val=Met—Gly—Ile=Ala—Asp—
Gly—Ala=Val—His—His—Asn—Thr—Glu—Glu—Ile=Val=Ala—Gln—Ser—Ile=Ala—Leu—Ser—
Ser—Leu=Met=Val—Ala—Gln—Ala=Ile=Pro—Leu—Val—Gly—Glu—Leu=Val—Asp—Ile—
Gly—Phe=Ala=Ala—Tyr—Asn—Phe=Val—Glu—Ser—Ile=Ile—Asn—Leu—Phe—Gln—Val=
Val—His—Asn—Ser—Tyr—Asn—Arg—Pro=Ala—Tyr—Ser—Pro—Gly—His—Lys—Thr—Gln—
Pro=Phe=Leu—His—Asp—Gly—Tyr—Ala=Val—Ser—Trp—Asn—Thr—Val—Glu—Asp—Ser—
Ile=Ile—Arg—Thr—Gly—Phe—Gln—Gly—Glu—Ser—Gly—His—Asp—Ile—Lys—Ile—Thr—
Ala—Glu—Asn—Thr—Pro=Leu=Pro=Ile=Ala—Gly—Val=Leu=Leu=Pro—Thr—Ile=Pro—Gly—
Lys—Leu—Asp—Val—Asn—Lys—Ser—Lys—Thr—His—Ile—Ser—Val—Asn—Gly—Arg—
Lys—Ile—Arg—Met—Arg—Cys—Arg—Ala=Ile—Asp—Gly—Asp—Val—Thr—Phe—Cys—
Arg—Pro—Lys—Ser—Pro=Val—Tyr—Val—Gly—Asn—

HA11DT is further characterized by the amino acid sequence:

```
                                                          —Gly—Arg—
                                                         /         \
Lys—Ile—Arg—Met—Arg—Cys—Arg—Ala—Ile—Asp—Gly—Asp—Val—Thr—Phe—Cys—

Arg—Pro—Lys—Ser—Pro—Val—Tyr—Val—Gly—(Asn—Gly)—Val—His—Ala—Asn—Leu—His—

Val—Ala—Phe—His—Arg—Ser—Ser—Ser—Glu—Lys—Ile—His—Ser—Asn—Glu—Ile—Ser—

Ser—Asp—Ser—Ile—Gly—Val—Leu—Gly—Tyr—Gln—Lys—Thr—Val—Asp—His—Thr—Lys—

Val—Asn—Ser—Lys—Leu—Ser—Leu—Phe—Phe—Glu—Ile—Lys—Ser—C
```

HA7DT is further characterized by the amino acid sequence:

—Gly—Val—His—Ala—Asn—Leu—His—

Val—Ala—Phe—His—Arg—Ser—Ser—Ser—Glu—Lys—Ile—His—Ser—Asn—Glu—Ile—Ser—

Ser—Asp—Ser—Ile—Gly—Val—Leu—Gly—Tyr—Gln—Lys—Thr—Val—Asp—His—Thr—Lys—

Val—Asn—Ser—Lys—Leu—Ser—Leu—Phe—Phe—Glu—Ile—Lys—Ser—C

HA3DT is further characterized by the amino acid sequence:

—Gly—Arg—

Lys—Ile—Arg—Met—Arg—Cys—Arg—Ala—Ile—Asp—Gly—Asp—Val—Thr—Phe—Cys—

Arg—Pro—Lys—Ser—Pro—Val—Tyr—Val—Gly—Asn—

Depending on the intended applications of the hydrolysis products, the conditions may be varied such that one or other truncated species predominates relative to the other species. Under other conditions, almost quantitative conversion of DT to both truncated DT species can occur. This may be important during purification. For example, for certain applications, equal or varying amounts of the two truncated species may be permissible thereby alleviating the need to purify one away from the other. It is within the scope of the present invention to include all preparations of modified DT wherein said preparations may or may not be pure, homogenous, or containing unhydrolyzed DT. The two modified DT will henceforth be referred to as HA48DT for the 48 Kd peptide and HA51DT or the 51 Kd peptide. The preparation of said modified DT is more fully described in Example 1 and by reference to FIG. 1.

Figure 2A:
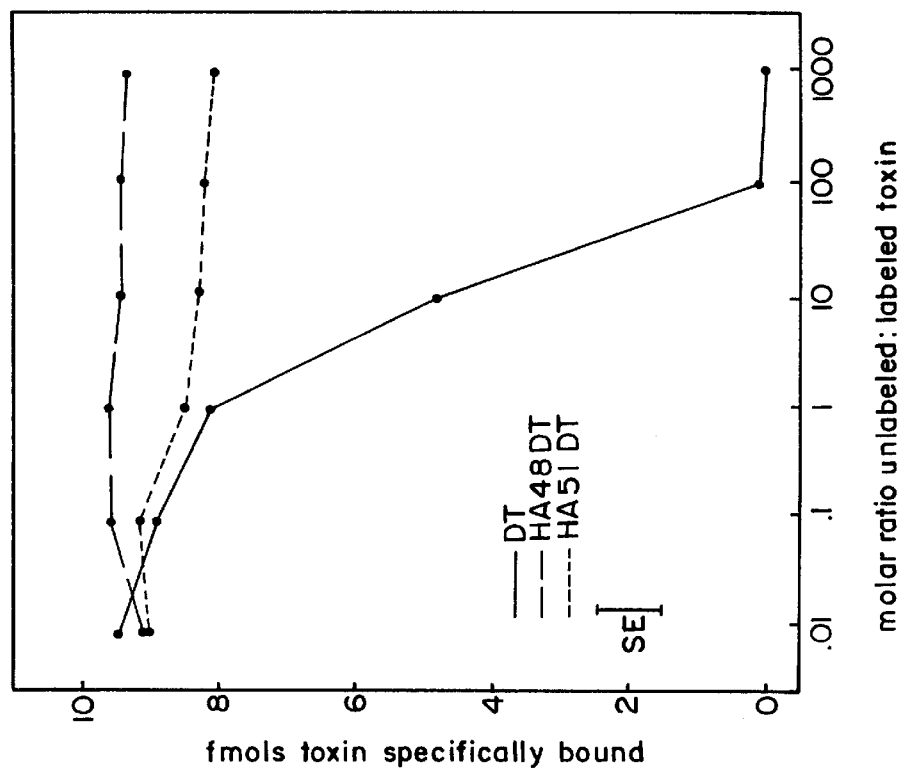

The primary diphtheria toxin membrane-binding property has been localized within a 17 Kd carboxy-terminal segment of the B-chain and apparently resides in a domain different from that responsible for the membrane translocation function. The translocation property has been partially ascribed to regions of hydrophobicity within the amino terminal 20 Kd of the B-chain. In accordance with the present invention and as described more fully in Example 2 and FIG. 2, the surprising discovery is made that the modified toxins HA48DT and HA51DT no longer possess the capacity to bind to target cells relative to native DT. One skilled in the art will immediately recognize the potential application of other hydrolyzing agents to effect a similar cleavage or the use of molecular biology to manipulate DNA encoding the DT such that a similar truncated DT is produced. A critical feature in this invention is the position of the cleavage and the functional properties of the resulting toxins. Accordingly, it is considered within the scope of this invention to include all hydroxyamine modified DT or similar DTs of same sequence wherein said toxins have lost the capacity for cell binding while retaining the property of translocation and the potential for full cytotoxicity. Furthermore, the scope of the subject invention also includes the carboxy terminal peptides comprising the binding region(s) of the DT molecule. Said peptides, defined herein as HA11DT, HA7DT and HA3DT, can be produced following hydroxyamine hydrolysis or by a variety of genetic engineering techniques.

In accordance with the present invention, the cytotoxic potential of the modified DT is exemplified by the chemical linking of a cell-binding moiety. The resulting hybrid molecule exhibited selective cytotoxicity by virtue of said cell-binding moiety. For the purposes of illustration, and in no way intended to limit the scope of the invention, the cell-binding moiety described in Example 3 is Concanavalin A (Con A). When chemically linked to Con A, HA51DT and HA48DT were much more potent cytotoxins than conjugates of Con A to diphtheria toxin A-chain (DTA; FIG. 3). Murine cells, such as the MLTC1 line used here, are insensitive to the effects of DT, but have fully susceptible elongation factor 2, providing a system for comparing toxicity of modified toxins to DT. Consequently, the cytotoxic effects of conjugates of Con A linked to either HA51DT or HA48DT to a conjugate of Con A linked to DT were directly compared. With both long (36 hour) and short (2 hour) term exposure of cells to conjugates, Con A-HA51DT was equally toxic as the conjugate of DT, while the HA48DT conjugate was only slightly less toxic than either conjugates of HA51DT or DT. These results indicates that DT, modified as described herein, possesses essentially all of the membrane transport ability of the original toxin, but little, if any, of the cell surface binding ability.

Con A is a protein that binds to mannosyl residues. Mannosyl residues are found as part of the cell surface gylcoproteins of many cells. In accordance with this invention, Con A was not intended to be exemplary of a selective cell-binding moiety but a model demonstrating the cytotoxic potential of the modified DT conjugates. Cell-binding moieties contemplated by the present invention wherein said moieties are linked to the truncated B-chain of HA48DT or HA51DT include antibodies, hormones (e.g. LH), other proteins, carbohydrates, and other compounds, which selectively bind to specific cells including cancer or tumour cells. Furthermore, either of the two modified DT can be chemically joined to a cell-specific moiety in a variety of ways. The linkers, most probably heterobifunctional reagents, can be varied to satisfy the requirements of individual applications. There are a large number of chemical reagents commercially available for this purpose and new ones can be synthesized to fit individual needs. Importantly, those described herein are merely illustrative and are not intended to limit the scope of the present invention. In the instant case, the heterobifunctional agent used was N-succinimidyl 3-(2-pyridyldithio) propionate, referred to herein as SPDP. The succinimidyl end reacts with amino groups and the pyridyldithio end reacts with sulhydryl groups.

The scope of the present invention should not be limited to any one cell-binding moiety or to any one method of linking said cell-binding moiety to the modified DT. The present invention also contemplates recombinant DNA techniques to link, at the level of DNA sequence, a binding moiety and a modified DT. In one instance, a gene encoding the binding moiety of, for example, an antibody or a hormone is fused using standard techniques to the carboxy terminal encoded end of the DNA coding for either HA48DT or HA51DT. The resulting hybrid gene, when transcribed and translated, will produce a hybrid protein comprising a cell-binding moiety linked to the modified DT. Techniques useful with respect to this aspect of the invention can be found in Silhavy et al., 1984. *Experiments with gene fusions.* Cold Spring Harbor Laboratory, pp. 1–293, hereby incorporated by reference.

The present invention also contemplates a method of producing an immunotoxin wherein said immunotoxin is selective for particular cell-types. It is contemplated that said cell types include cancer, tumors, lymphomas and cell abberation diseases. The immunotoxin can be prepared in accordance with the present invention by linking, via chemical or molecular means, a cell-binding moiety to HA48DT or HA51DT and using said immunotoxin as selective cytotoxic agents in vivo. Consequently, the potential applications are as myriad as the applications of selective cell killing. Listed below are some of the applications for these peptides that may be considered useful.

1. Antibiotics for the treatment of tumors, i.e. anticancer agents.
2. Antibiotics for the treatment of virus diseases, i.e. antiviral agents.
3. Antiparasite agents.
4. Agents to facilitate organ transplantation, i.e. specific anti-immune agents.
5. Agents to prevent graft vs. host disease, i.e. specific anti-immune agents.
6. Treatment for autoimmune diseases, i.e. specific anti-immune agents, and for related illnesses such as multiple sclerosis, muscular dystrophy, arthritis, and some forms of diabetes.
7. Treatment for hyperplasis disorders.
8. Treatment for obesity, or simply cosmetic fat reduction.
9. Treatment of meat animals to produce lower fat products.
10. Regulation of hormonal activities, including reproductive regulation and castration.
11. Treatment of plants to facilitate hybrid production.
12. Direction of embryonic development in animals. It is, therefore, within the scope of this invention to include pharmaceutical (i.e. therapeutic) preparations of said immunotoxins, as well as others.

The active ingredients of the therapeutic compositions and the modified DT molecule slinked to a cell binding moiety of the present invention will exhibit excellent anticellular including anticancer activity. Thus the active ingredients of the therapeutic compositions and the novel compounds of the present invention are contemplated to inhibit transplanted mouse tumor growth and induce regression and/or palliation of leukemia and related cancers in mammals when administered in amounts ranging from about 1 ug to about 20 mg per kilogram of body weight per day. A preferred dosage regimen for optimum results will probably be from about 10 ug to about 20 mg per kilogram of body weight per day. This dosage regimen may be adjusted to provide the optimum therapeutic response. For example, several divided doses may be administered daily or the dose may be proportionally reduced as indicated by the exigencies of the therapeutic situation.

The active compounds may also be administered parenterally or intraperitoneally. Under ordinary conditions of storage and use, these preparations contain a preservative to prevent the growth of microorganisms.

The pharmaceutical forms suitable for injectable use include sterile aqueous solutions. In all cases the form must be sterile and must be fluid to the extent that easy syringability exists. It must be stable under the conditions of manufacture and storage and must be preserved against the contaminating action of microorganisms such as bacteria and fungi. The carrier will be aqueous solutions. The preventions of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Sterile injectable solutions are prepared by incorporating the active compounds in the required amount in the appropriate solvent followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 5 ug to about 10 mg, with from about 250 ug to about 750 ug being preferred. In the case of compositions containing supplementary active ingredients, the dosages are determined by reference to the usual dose and manner of administration of the said ingredients.

Regression and palliation of some cancers are contemplated, for example, using intraperitoneal administration. A single intravenous dosage or repeated daily dosages can be administered. Daily dosages up to about 5 days will probably be sufficient. It is also possible to dispense one daily dosage or one dose on alternate or less frequent days. As used herein, cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

The present invention is further illustrated and defined by the following examples, but said examples should not be construed to limit the scope of the subject invention.

EXAMPLE 1

Purification of diphtheria toxin

DT was purified by DEAE-sephacel ion-exchange chromatography. A column of DEAE-sephacel (2.0×10 cm) was equilibrated in 0.01M Tris-HCl, pH 7.7 containing 1 ug/ml phenymethyl sulfonyl fluoride (PMSF) and 0.02% sodium azide. DT was absorbed to the column in the buffer used for equilibration buffer, and eluted with a gradient of 0 to 0.4M NaCl in the equilibration buffer. Fractions corresponding to DT, as judged by SDS-PAGE and cytotoxicity, were pooled and dialyzed (4 C.; 12 hours) against 0.01M Tris-HCl, pH 8.2 containing 1 ug/ml PMSF. Following dialysis, DT was concentrated (50 mg/ml) with Centricon microconcentrators and stored at −80 C. DT concentrations were determined by utilizing an extinction coefficient of 1.19 (280 nm).

Hydroxylamine cleavage of diphtheria toxin

Hydroxylamine cleavage of DT was performed as follows. A solution of 2M hydroxylamine, 6M quanidine-HCl, pH 9.0 (4.5M LlOH as titrant) was added at room temperature to DEAE-purified DT so that the final concentration was 170 uM DT, 5.4M quanidine-HCl and 1.8M hydroxylamine. The mixture was reacted at 38°–40 C. for 8 hours with occasional stirring, and the reaction stopped by chromatography with Biogel P6-DG (2×18 cm) equilibrated in deionized, glass fiber filtered 6M urea, 0.1M Tris-HCl, 0.001M ethylenediaminetetracetic acid (EDTA, desalting buffer), pH 8.2. DT A-chain was reacted under identical conditions. Control reactions were performed in which conditions remained the same with omission of hydroxylamine.

To remove small peptides, the reacted toxin was chromatographed through a column of Sephadex G-75 superfine (2×80 cm) equilibrated in desalting buffer. The high molecular weight peak was renatured by chromatography through a column of Biogel P6-DG (2×30 cm) equilibrated in 0.05M Tris-HCl, 0.001M EDTA, pH 7.7, containing 1 ug/ml PMSF (renaturation buffer) to remove the urea. The toxin was concentrated as described above, and applied to a Pharmacia (Uppsala, Sweden) FPLC, Superose 6 column (HR 10/30; 10×60 mm) equilibrated in 0.05M Tris-HCl, pH 7.7, containing 1 ug/ml PMSF (purification buffer). Fractions containing monomer toxin were pooled and applied to a Pharmacia FLPC Mono-Q anion exchange column (HR 5/5; 5×50 mm) equilibrated in purification buffer. The toxin was eluted with a gradient of 0 to 0.3M NaCl in purification buffer. As judged from chromatograms and sodium dodecyl sulfate-polyacrylamide gel electrophoresis (SDS-PAGE), fractions enriched in unreacted diphtheria toxin, 51 Kd DT (HA51DT) and 48 Kd DT (HA48DT) were pooled separated and rechromatographed over the FPLC Mono-O column utilizing the similar conditions. A single major chromatogram peak corresponding to fractions containing essentially pure DT (as judged by SDS-PAGE) or modified toxin was obtained for each of the three proteins. The DT were stored at −80 C. until further use.

SDS-PAGE

SDS-polyacrylamide gel electrophoresis was performed on 10 to 15% gradient gels utilizing a Pharmacia Phast-Gel™ system. Silver straining was performed on all gels.

Molecular Sieve Chromatography

Parmacia Past Performance Liquid Chromatography (FPLC) Superose 6 (equilibrated with 0.05M Tris HCl, 0.001M EDTA; pH 7.7) was utilized to determine degree of aggregation of toxins at neutral and low pH (4.5). Absorbance of the column effluent was monitored at 280 nm. All samples were filtered through a 0.22 um filter prior to injection.

Biological Properties of Hydroxylamine-Cleaved Toxins

In vitro Translation: Inhibition of protein synthesis was measured using a myeloma cell (Sp2/0; American Type Culture Collection, Rockwell, Md.) lysate. Briefly, the reaction mixture contained 1.8 ml of cell lysate, 15 mM ATP, 2.8 mM GTP, 25.4 mg of creatine phosphate/ml, 2 mg creatine kinase/ml solution, 0.18 ml of amino acid solution (without leucine), and 65 ul of [3H] leucine. Final volume was 2 ml; 80 ul was utilized for measurement of protein synthesis.

Binding of $^{125}$I Diphtheria Toxin to Cell Membranes

DT was iodinated by the iodogen method to a specific activity of 0.709 ucl/pMole toxin. Membranes were prepared from human breast cancer cells (MCF-7, Michigan Cancer Foundation, Detroit, Mich.) determined to be sensitive to diphtheria toxin. MCF-7 cells were cultured in Dulbecco's Minimum Essential Media supplemented with 5% fetal calf sera (FCS, Hycione, Inc., Logan Utah) 250 ug/ml gentamycin, pH 7.6; in 75 cm$^{-1}$ flasks in an atmosphere of 5% CO; upon reaching confluency the cells were gently mechanically harvested and transferred to 0.25M HEPES (H-2-Hydroxyethylpipazine-N'-2-Ethanesulfonic Acid), 0.01 sucrose 0.1% (w/v) bovine serum albumin (BSA); pH 7.4. The cells were broken by 25 strokes of a loose fitting dounce homogenizer and the homogenate centrifuged at 30,000 G for 30 min at 4 C. The resulting pellet was resuspended in 0.1M HEPES, 0.001 m CaCl$_2$; pH 7.4 and centrifuged at 30,000×G for 30 min at 4 C. Upon completion the pellet was resuspended in DMEM containing 0.025M HEPES, 0.1 BSA (pH 7.5). Binding was conducted on membranes representing 1×10 cells in 100 ul buffer. Iodinated toxin and unlabelled proteins were added in 50 ul 0.025M HEPES, 0.1% (w/v) BSA (pH 7.5). Binding was determined after a 12 hour incubation at 4 C. Following addition of 3 ml ice-cold (HEPES) buffer, excess label was removed by centrifugation at 30,000×G for 10 min. at 4 C., and decanting the supernatant. Specific binding was calculated as the amount of iodinated toxin displaceable by a 1000-fold molar excess of unlabeled diphtheria toxin.

ATP-Affinity Chromatography

Nucleotide affinity chromatography (ATP [C8]-Agarose, 1 ml column) was performed as follows: Monomer toxins were applied in 0.01M sodium phosphate; pH 7.5 and the column washed until the absorbance of 0.5 ml fractions returned to baseline. Protein was eluted from the column with 0.5M NaCl in start buffer.

Cytotoxicity of Diphtheria Toxin and Hydroxyamine Cleaved Toxins

Cytotoxicity was determined utilizing MCF-7 cells cultured as described above. Cells were plated at 5000 cells per well (200 ul) in 96 well polystyrene culture plates. After allowing 48 h for plating, the cells were washed twice with phosphate buffered saline (PBS, pH 7.2), and toxins added in media (n=8 wells/treatment). Cells were cultured at 37 C. for 36 h in the presence of toxins. Following culture, cytotoxicity as expressed in cells surviving, was determined by acid phosphatase activity as previously described (Connolly et al., 1985 *J. Anal. Biochem.* 152:136–140).

Preparation and Cytotoxicity of Hybrid Proteins Containing Hydroxylamine Cleaved Diphtheria Toxin DT and hydroxylamine cleaved toxins were equilibrated in PBS (pH 7.5). DT chain was prepared as described by (Bumol et al., 1983. *Proc. Natl. Acad. Sci., USA.* 80:529–533), and reduced for 10 min in the presence of 10 mM dithiothritol prior to conjugation. Reductant was removed by chromatography through Sephadex G-25 (1.5× 20 cm) equilibrated with PBS. Luteinizing hormone and Con A were brought into solution in PBS from lyophilized stocks.

Conjugation to Luteinizing Hormone and Con A

A procedure modified from Guillemont et al., (1985. *J. Cell. Physiol.* 122:193–199) for derivatization, and conjugation of Con A to DT with N-succinimidyl 3-(2-pyridyldithio) propionate (SPDP) was utilized for all proteins. SPDP (40 mM stock in absolute ethanol) was reacted with protein (in PBS) in the conditions summarized in Table 1, for 60 min. at room temperature and the reaction stopped by dialyzing overnight at 4 C. against 4 L PBS; pH 7.5. For conjugation to PDP-containing DT and hydroxylamine cleaved toxins, LH and Con A were reduced with 10 mM dithiothritol for 10 min at room temperature and desalted (Sephadex G-25; equilibrated in PBS). Con A or LH were reacted with each toxin protein at a 1:1 molar ratio for 6 h at 23 C. followed by 12 h at 4 C. The extent of conjugation was followed spectrophotometrically at 343 nm. The reactions were stopped by dialyzing into PBS at 4 C. overnight. For a summary of the conjugation see Table 1.

Cytotoxicity Assays

Mouse Leydig tumor cells (MLTC 1) were maintained in RPMI culture media buffered with 0.025M HEPES, 0.025M sodium bicarbonate, with 250 ug/ml gentamycin sulfate and 5% (v/v) fetal calf serum; pH 7.7. The cells were grown in 75 cm$^2$ flasks in an atmosphere of 5% CO2 (37 C.) and harvested on day 3 post-plating for all studies. On the day prior to addition of toxins the cells were plated in 96 well plates at 5000 cells per well in 200 ul media. On the day of the assay, cells were washed twice with PBS prior to the addition of treatments in media. For a determination of cytotoxicity, cells were cultured for 24 h (LH conjugates) or 36 h or the Con A conjugates. Kinetics of toxicity was determined for toxin derivatives of Con A. After two hours in the presence of conjugates, cells were washed twice with media to remove toxins, and cultured fro the remainder of 36 hours in the absence of conjugates. Cell number was determined by acid phosphatase assay (Connolly et al., supra). Differences in toxicity between proteins were determined by analysis of variance.

TABLE 1

CONJUGATION OF TOXINS TO CELL RECOGNITION MOIETIES

| PROTEIN | CONCEN-TRATION MG/ML | MOLAR RATIO SDP:PROTEIN[1] | MOLES PDP/ PROTEIN[2] | MOLES LIGAND/ TOXIN[3] |
|---|---|---|---|---|
| (Conjugation of Con A to toxins) | | | | |
| CON A | 1.0 | 5 | 2.01 | — |
| DT | 1.0 | 2 | 1.12 | 1.06 |
| HA51DT | 0.5 | 2 | 0.9 | 0.87 |
| AH48DT | 0.5 | 2 | 1.31 | 1.23 |
| DTA | 1.0 | — | — | 0.91 |

[1] SPDP was reacted with each protein at the given protein concentration and molar excess SPDP;
[2] Moles pyridyl dithio propionate incorporated into each protein with the given conditions;
[3] Moles of Con A incorporated into each toxin molecule.

All proteins except DTA were reacted with SPDP as described in the text to introduce PDP moieties into protein. For conjugation to diphtheria toxin, HA51DT and HA48DT, Con A-PDP was reduced. For conjugation to DTA, PDP containing ligand was used.

EXAMPLE 2

The following example describes the generation of HA48DT and HA51DT following hydroxyamine hydrolysis.

Two carboxy-terminal truncated forms of DT were prepared by specific chemical proteolysis with hydroxylamine. The proteolysis is specific for either of two asparaginyl-glycyl peptide bonds near the carboxy terminal and results in the generation of two new proteins by removal of 81 and 53 amino acids from the carboxy terminal end (FIG. 1). Purified, quanidine-denatured DT was reacted with alkaline hydroxylamine to break asparaginyl-glycyl peptide bonds. Controlled reaction conditions resulted in the production of the two proteolysis products of 51 Kd (HA51DT) and 48 Kd (HA48DT) Mr, as well as unreacted DT in approximately equal proportions. The liberated carboxy-terminal peptides of DT were removed by molecular sieve chromatography under denaturing conditions, following which the hydroxylamine cleaved proteins were renatured and monomer protein was isolated by molecular sieve chromatography. The final isolation of the modified proteins was performed by anion-exchange chromatography. Purity of the modified proteins was demonstrated by SDS-PAGE.

EXAMPLE 3

The following example tests the cytotoxicity of HA48DT and HA51DT.

Neither of the two modified proteins, HA51DT or HA48DT, are toxic for DT-sensitive cells (MCF-7) at concentrations up to 10,000 fold greater when compared with DT, nor do the modified toxins, at 1000-fold molar excesses, compete with DT for binding to cell membranes prepared from these cells (FIG. 2). DT was labeled with iodogen to a specific activity of 0.071 uCi/pmol protein. Binding was performed in 17×75 cm polypropylene test tubes on membranes from $1\times10^7$ cells in 150 ul 0.05M HEPES, 0.1% BSA (pH 7.5; HEPES buffer) during a 12 h incubation at 4 C. To each aliquot of membranes 40,000 cpm of 125-I DT was added with the indicated concentration of non-iodinated protein. Membranes were precipitated by centrifugation (30,000×g) of the contents of the tubes after addition of 3 ml ice-cold HEPES buffer; radioactivity in the pellet was determined after removal of the supernatant. Non-specific binding was determined as the amount of labeled toxin displacable by a 1000-fold excess unlabeled toxin. Each points represents an average of 3 replicates; pooled standard error is indicated.

Toxicity of DT, HA51DT and HA48DT to MCF-7 cells was determined as follows. Cells were maintained in Delbecco's minimum essential media containing 5% fetal calf serum (DMEM). For the toxicity experiments, cells were plated at 5000 cells/well in 200 ul DMEM in 96 well polystyrene microtiter plates. Toxicity was expressed as a percentage of (control) cells surviving after 36 h culture as determined by acid phosphatase activity (Connolly et al., supra). The assay for acid phosphatase is highly correlated (r=0.96) to exclusion of trypan blue as a method for determining cellular death induced by toxins. For both FIGS. 2(a) and (b), each point represents a mean of 8 observations; pooled standard error is given.

EXAMPLE 4

The following example describes the cytotoxicity of hybrid DT molecules.

Figure 3B:
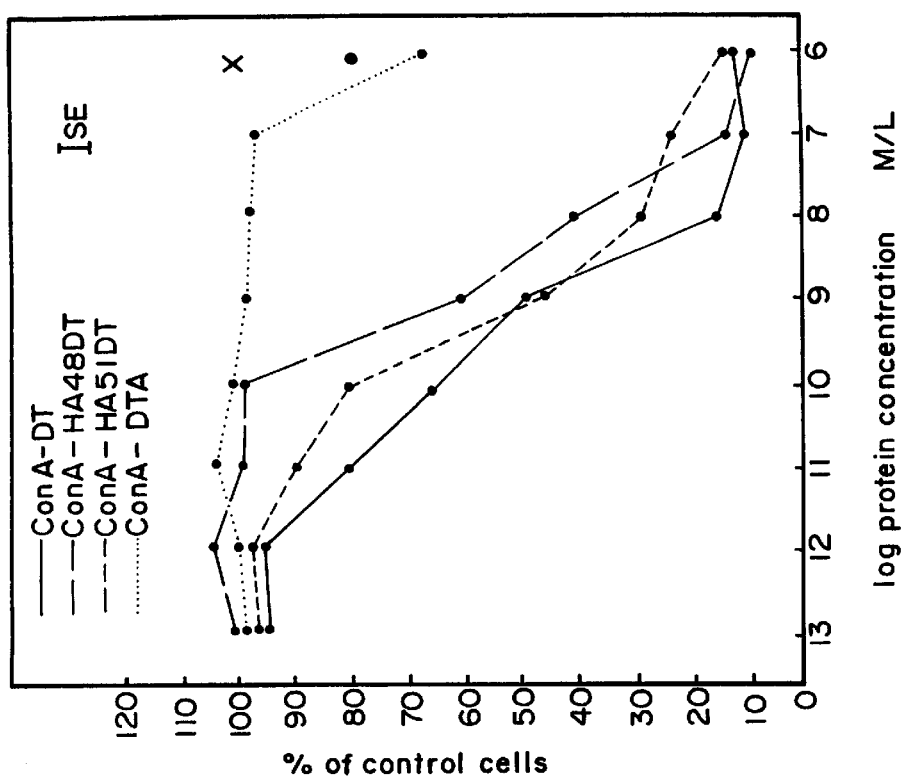
FIG. 3 represents cytotoxicity of hybrid toxins prepared with DT, HA51DT, HA48DT and the A-chain of DT. Graph (a) represents cytotoxicity of Con A hybrid toxins on mouse Leydig tumor cells (MLTCl) following exposure to toxins for 36 hours; graph (b) represents cytotoxicity of Con A hybrid toxins on MLTCl cells following two hour exposure to toxins.
Figure 3A:
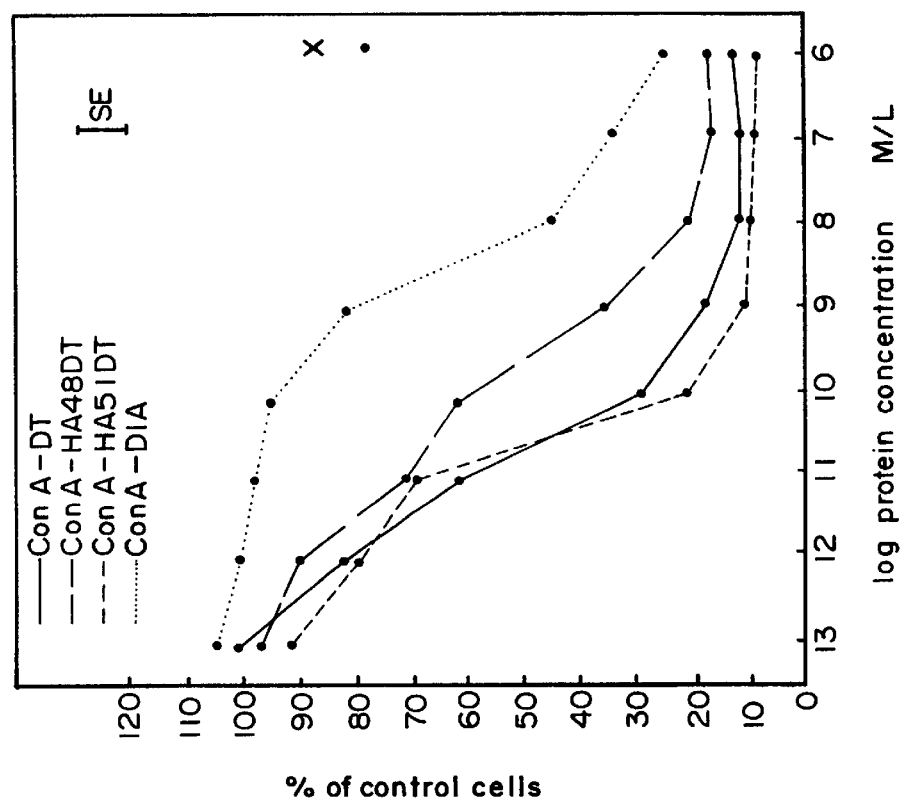

When chemically linked to a cell surface binding moiety, Concanavalin A (Con A), HA51DT and HA48DT are much more portent cytotoxins than conjugates of Con A to diphtheria toxin A-chain (DTA; FIG. 3). Pyridyl dithiopropionate (PDP) groups were introduced into concanavalin A (Con A), DT, HA51DT, HA48DT with the heterobifunctional linking reagent SPDP (N-succinimidyl 3-(2-pyridyldithio) propionate; Sigma) (Guillemot et al., 1985. *J. Cell. Physiol.* 122:193–199; Gilliland et al., 1978. i Proc. Natl. Acad. Sci., USA 75:5319–5323). Briefly, SPDP (40 mM stock solution in absolute ethanol) was reacted at the given ratios with Con A (f:1) DT (2:1), HA51DT (2:1), and HA48DT (2:1) in 0.01M phosphate, 0.186M sodium chloride; pH 7.5 (PBS) for 60 min at 23 C. The reactions were halted and unreacted SPDP removed by dialysis for 12 hours at 4 C. against 4 L PBS. For conjugation to PDP-containing DT, and HADT's, Con A was reduced with 10 mM dithiothreitol to generate a reactive thiol, and reacted separately with PDP-DT, PDP-HA51DT, and PDP-HA48DT at a 1:1 molar ratio for 6 h at 23 C. and 12 hours at 4 C. For conjugation of Con A to DTA, prepared as previously described (Bumol et al., 1983. *Proc. Natl. Acad. Sci., USA* 80:529–533), PDP-Con A was reacted with A-chain at a 1:1 molar ratio. The extent of all reactions was determined spectrophotometrically by measuring liberation of pyridyl-2-thione release at 343 nm during the thiol-disulfide exchange reaction. The cytotoxicity of Con A hybrid toxins on mouse Leydig tumor cells (MLTCl) was observed following exposure to toxins for 36 hours (FIG. 3a). Cells were plated in 96 well polystyrene microtiter plates at 5000 cells/well in 200 ul DMEM, and conjugates added. After 36 hours continuous culture in the presence of hybrids, the cell number was determined. In FIG. 3(b) the cytotoxicity of Con AS hybrid toxins on MLTCl cells is shown following 2 hour exposure to toxins. Cells were cultured in the presence of toxins for 2 hours after which the cells were washed free of toxin and cultured through 36 hours at which time the cell number was determined.

Murine cells, such as the MLTCl line used above, are insensitive to the effects of DT, but have fully susceptible elongation factor 2, providing a system for comparing toxicity of modified toxins to DT. Consequently, the cytotoxic effects of conjugates of Con A linked to either HA51DT or HA48DT to a conjugate of Con A linked to DT were directly compared. With both long (36 hours) and short (2 hours) term exposure of cells to conjugates, Con A-HA51DT was equally toxic as the conjugate of DT, while the HA48DT conjugate was only slightly less toxic than either conjugates of HA51DT or DT. These results indicate that DT, modified as described herein, possesses essentially all of the membrane transport ability of the original toxin, but little, if any, of the cell surface binding ability. Differences in toxicity of the hybrids based on the $LD_{50}$ is summarized in Table 2.

TABLE 2

CYTOTOXICITY OF DIPHTHERIA TOXIN DERIVATIVES 1) 36 HOUR CONTINUOUS CULTURE
WITH CON A-TOXIN CONJUGATES:

| CON A-TOXIN | $LD_{50}$ (pM) | EFFECTIVENESS RELATIVE TO CON A-DTA |
|---|---|---|
| DTA | 8,400 | 1 |
| HA48DT | 270 | 31 |
| HA51DT | 25 | 336 |
| DT | 21 | 400 |

2) TWO HOUR PULSE
WITH CON A TOXIN/36 HOUR CULTURE WITHOUT TOXIN:

| CON A-TOXIN | $LD_{50}$ (nM) | EFFECTIVENESS RELATIVE TO CON A-DTA |
|---|---|---|
| DTA | 3,500 | 1 |
| HA48DT | 3.5 | 1,000 |
| HA51DT | 0.74 | 4,730 |
| DT | 0.94 | 3,720 |

EXAMPLE 5

The following example describes the production of an antibiotic to the AIDS virus utilizing the cytotoxic agents HA48DT or HA51DT.

The T-lymphocyte antigen CD-4 appears to be the cellular receptor for the HIV virus, the pathogen causing AIDS [Littman, D. R., Ann. Rev. Immun. 5, 561, 1987]. Considerable variation of the HIV virus has been noted, but all infective forms bind to CD-4 through the viral gp 120 envelope protein [e.g. Lasky et al., cell 50, 975, 1987]. Consequently, the use of CD-4 to recognize HIV-infected cell avoids the problem of viral antigenic variation that is presently one of the major problems in vaccine production. Cloned, soluble forms of CD-4 are available [e.g. Fisher et al., Nature 331, 76, 1988]. Toxins joined to CD-4 have been shown to kill HIV-infected cells selectively [Till et al., Science 242, 1166, 1988; Chaudhary et al., Nature 335, 369, 1988].

A major drawback in the development of specific cytotoxic agents has been the slow kinetics of killing offered by most currently available conjugates. Those specific cytotoxic agents appear to be sufficiently selective, but cytotoxic potency appear to be too low for effective use in vivo. The truncated diphtheria toxins lack intrinsic HA48DT or HA51DT binding properties, but, when attached to a cell-binding agents, are as potent as the original toxin [Myers and Villemez, J. Biol. Chem. 263, 17122, 1988]. Experiments in model systems indicate that toxic moieties of that potency will be sufficient for in vivo effectiveness [Marsh, J. A., J. Biol. Chem. 263, 15993, 1988; Pastan et al., Cell 47, 641, 1986].

An antibiotic for the treatment of AIDS can be produced by linking soluble CD-4 to either of the truncated diphtheria toxins, HA48DT or HA51DT. The covalent bond between CD-4 and the truncated toxins can be either a disulfide, a thioether, or a sterically restricted disulfide linkage, all of which have been shown to produce effective selective cytotoxic agents with these types of toxins.

EXAMPLE 6

The following example describes the production of an antibiotic for treatment of melanoma using HA48DT or HA51DT.

There exists an antibody which binds selectively to a large molecular weight cell surface molecule found in more than two-thirds of human melanoma tumors, and not to normal cells [Spitler, L. E., "Immunotoxins", A. E. Frankel ed., Kluwer Acad. Pub., 1988, Chap. 26]. The A-chain of ricin joined to this antibody has been shown to kill melanoma cells selectively. Clinical trials using the melanoma-specific antibody conjugated to ricin A-chain, tradenamed Xomazyme-Mel, has proved to have few side effects. While some of the human tumors have regressed somewhat, the patients in these clinical trials have gone largely uncured.

One of the major drawbacks in the development of specific cytotoxic agents has been the slow kinetics of killing offered by most currently available conjugates. Those specific cytotoxic agents appear to be sufficiently selective, but cytotoxic potency appears to be too low for effective use in vivo. However, HA48DT or HA51DT, when attached to a cell-binding agent, are as potent as the original toxin [Myers and Villemez, J. Bio. Chem. 263, 17122, 1988]. Experiments in model animal systems indicate that toxic moieties of that potency will be sufficient for in vivo effectiveness [Marsh, J. A., J. Biol. Chem. 263, 15993, 1988; Pastan et al., Cell 47, 641, 1986].

New antibiotic for the treatment of melanoma can be produced by linking the Xoma anti-melanoma antibody, or the f(ab) fragment of the antibody, to either of the truncated diphtheria toxins, HA48DT or HA51DT. The covalent linkage between the antibody and the truncated toxins could be a disulfide, a thioether, or a sterically restricted disulfide linkage, all of which have been shown to produce effective selective agents with these types of toxins.

What is claimed is:

1. A process for preparing a 51, 48, 11, 7 or 3.5 kilodalton peptide fragment from a diphtheria toxin which comprises subjecting said toxin to chemical proteolysis to cleave said toxin at either or both the asparaginyl-glycyl peptide bonds thereby producing at least two of HA51DT, HA48DT, HA11DT, HA7DT and HA3DT peptide fragments, wherein said HA51DT and HA48DT peptide fragments have cytotoxic and translocation activity and lack cell binding activity; and recovering said at least two produced fragments.

2. The process according to claim 1 in which the proteolysis is accomplished with hydroxylamine.

3. The process of claim 1 wherein subjecting said toxin to chemical proteolysis comprises:
   (a) denaturing said toxin to produce a denatured toxin;
   (b) treating said denatured toxin with hydroxylamine for a time and under conditions to effect said proteolysis;
   (c) renaturing said at least two produced fragments; and
   (d) recovering said at least two produced fragments.

4. The process of claim 3 which comprises:
   (a) separating any of said HA11DT, HA7DT and HA3DT peptide fragments from any of said HA51DT and HA48DT peptide fragments after said proteolysis;
   (b) renaturing any of said HA51DT and HA48DT peptide fragments; and
   (c) recovering any of said HA51DT and HA48DT peptide fragments such that any of said peptide fragments recovered are substantially devoid of intrinsic binding activity.

* * * * *

UNITED STATES PATENT AND TRADEMARK OFFICE
CERTIFICATE OF CORRECTION

PATENT NO. : 5,827,934
DATED : October 27, 1998
INVENTOR(S) : C. L. Villemez, et al.

It is certified that error appears in the above-identified patent and that said Letters Patent are hereby corrected as shown below:

On The Title Page: Insert --[30] FOREIGN APPLICATION PRIORITY DATA:

| | | |
|---|---|---|
| Australia | 31103/89 | 3/8/89 |
| Canada | 593101 | 3/8/89 |
| Denmark | 436/89 | 3/8/89 |
| EPO | 89104119.6 | 3/6/89 |
| Ireland | 751/89 | 3/8/89 |
| Israel | 89504 | 3/6/89 |
| Japan | 53970/1989 | 3/7/89 |
| Portugal | 89927 | 3/7/89-- |

On The Title Page, [56] References Cited, OTHER PUBLICATIONS:

Delete one instance of --Kaczorek et al. (1983) Science 221, 855-858.

-- and --Bornstein et al. (1977) Meth, Enzymol.47, 132-145.--

Column 11, Line 52: "molecule slink" should read --molecules link--

UNITED STATES PATENT AND TRADEMARK OFFICE
CERTIFICATE OF CORRECTION

PATENT NO. : 5,827,934

DATED : October 27, 1998

INVENTOR(S) : C. L. Villemez, et al.

It is certified that error appears in the above-identified patent and that said Letters Patent is hereby corrected as shown below:

Column 17, Line 7: "portent" should read --potent--

Signed and Sealed this

Fifteenth Day of May, 2001

Attest:

NICHOLAS P. GODICI

Attesting Officer    *Acting Director of the United States Patent and Trademark Office*